Jan. 9, 1973 H. A. JOHNSON, JR Plant Pat. 3,286
STRAWBERRY PLANT
Filed April 8, 1971
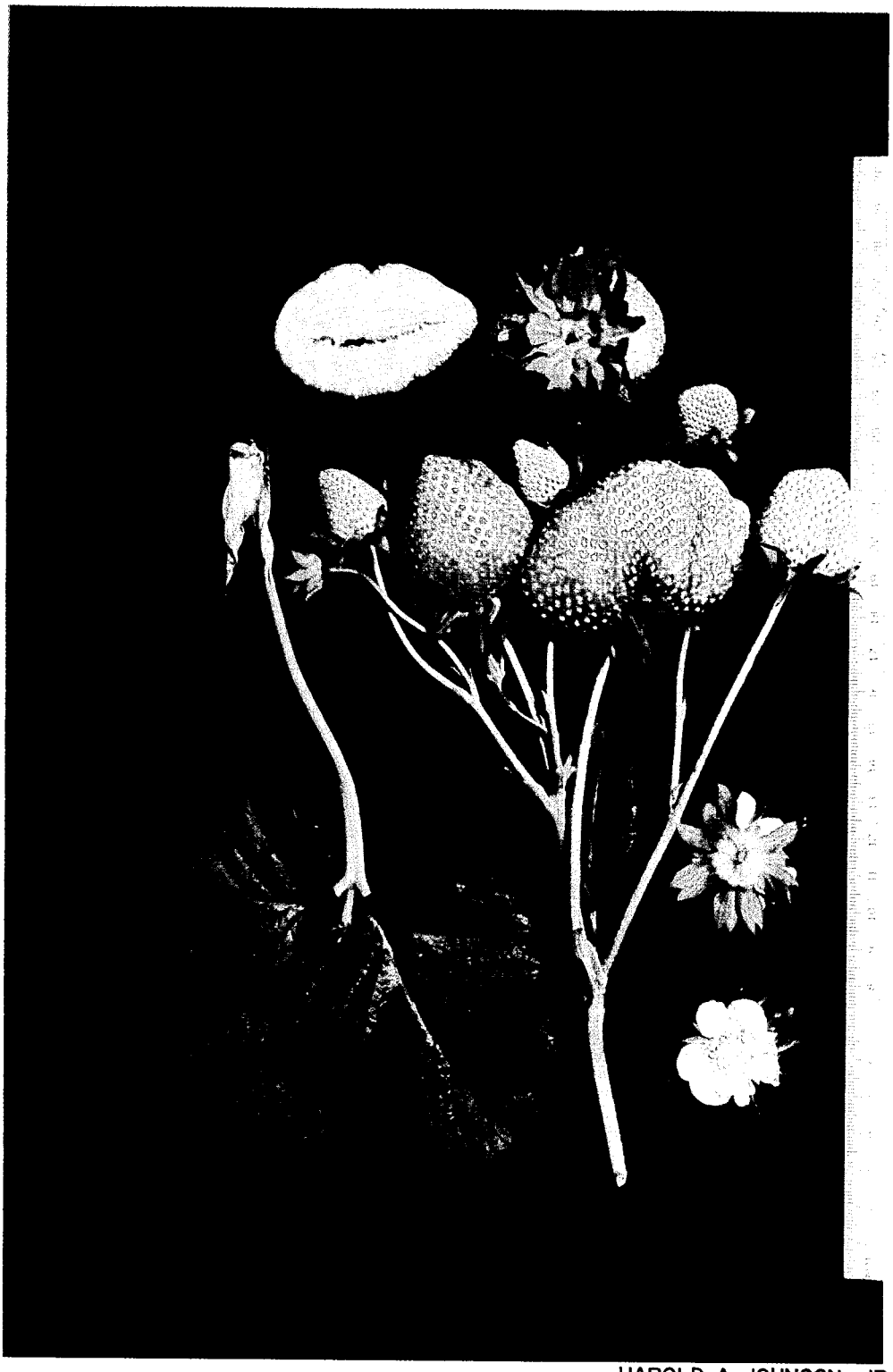
HAROLD A. JOHNSON, JR.
Townsend and Townsend United States Patent Office Plant Pat. 3,286

Patented Jan. 9, 1973

3,286

STRAWBERRY PLANT

Harold A. Johnson, Jr., Watsonville, Calif., assignor to Driscoll Strawberry Associates, Inc., Watsonville, Calif.

Filed Apr. 8, 1971, Ser. No. 132,620
Int. Cl. A01h 5/03
U.S. Cl. Plt.—49 1 Claim This invention relates to a new and distinct variety of strawberry plant which is the result of a cross of the patented everbearing variety known to The Strawberry Institute of California as Selection E3, Patent No. 2,891, and The Strawberry Institute of California Selection NM55.5.

The seedlings resulting from the aforementioned cross were grown and asexually multiplied in Shasta County, Calif., and tested in the fruiting beds on the property of growers of the Driscoll Strawberry Associates, Inc. Clones of the seedlings were also held at the Propagation Nursery in Shasta County. One plant was selected from the aforementioned group of seedlings and further asexually reproduced in the Shasta County nursery of Driscoll Strawberry Associates, Inc. Tests followed in various parts of California during intervening seasons on various properties of grower members of the Driscoll Strawberry Associates, Inc. These tests indicated the merits of the novel plant and resulted in its selection as a promising test variety.

Plant parts of the new variety, typical in size, shape and color are pictured in the accompanying photograph. The inflorescence of this new variety varies considerably in the way it branches, but the inflorescence illustrated is typical of most branching during the month of June. A primary berry illustrated is short wedged, considerably wider than long, while the secondary berry is medium wedged. The illustration shows a pedicel holding a secondary berry originating directly from the axil with only one tertiary pedicel branching from it. Often this secondary pedicel produces one single secondary berry without any branching from it. The leaf shown is typical in appearance and size and the flower is also typical of primary and secondary flowers during this period of the year.

The novel plant is medium in size, vigorous and is conspicuous because of its dark glossy rugose foliage. The transplant is comparatively large as it comes from the nursery and produces a vigorous young plant early in the spring with a strong crown crop generally resulting. It is a spring variety, but has the ability of uniform production during the first year after being planted unless the transplant receives an excessive chilling before being planted. The primary berries from the crown crop and the main crop are large and showy with an excellent gloss. Subsequent crops have fruit that remains medium to large in size, with considerable variation in fruit shape, but all fruit has a dark high gloss appearance. The crown crop may commence during late March in southern California in first year winter plantings. The crop is continuous with some peaks and valleys in production during the summer and fall. The crop during the second fruiting year as well as the spring crop from summer set plants starts fruiting in early to mid-May, with uniform production that continues throughout the late spring, summer and fall periods.

The plant of the present invention is distinguished from other varieties by its flowers, fruit and plant characteristics. If given proper chilling before being planted, the plant is vigorous enough to support a large crop the first year after a winter planting. Production is also good during the second fruiting year. The plant of this new variety is generally not larger than the Goldsmith variety, Plant Patent No. 1,735. The leaflet size is generally larger than Goldsmith, and the plant is darker and the leaflets more rugose with deeper, more vivid serrations at the apex. The petioles are normally heavier and produce an abundance of bracts growing from the petioles in contrast to Goldsmith. During much of the year the petiole length of the new variety is shorter than that of Goldsmith. The leaflet shape of the new variety is distinct inasmuch as it is ovate at the apex. The petiolules are generally longer than that of Goldsmith.

The plant remains dark throughout the season with multiple crowns forming by the end of the first growing year. If given equal amounts of chilling during the winter of planting, Goldsmith is less likely to produce excessive vegetative growth and runners. Therefore, the new variety should be dug at the nursery with less chilling than Goldsmith and transplanted sooner. The plant size the second growing year is often small, but compact with multiple crowns producing an abundance of inflorescences per plant during the entire second year. The inflorescence the first fruiting year is usually equal to Goldsmith in total length, but individual peduncles and pedicels are thicker on the new variety. Branching is similar to Goldsmith inasmuch as most of the pedicels holding the primary berry originate from the axil formed by secondary peduncles. The branching of the new variety is peculiar in that often the peduncles holding secondary berries have only one or no pedicels branching from them which is in contrast to Goldsmith and most varieties which have at least two pedicels originating from the secondary peduncle. Often secondary peduncles become pedicels inasmuch as there is no branching at all from them.

Secondary and primary berries often ripen simultaneously. The diameters of flowers are quite large, often larger than Goldsmith and there are generally more petals per flower than Goldsmith. The fruit of this variety is large and showy normally with a dark glossy and quite firm and as a rule firmer than Goldsmith. The fruit shape of this new variety varies considerably. Usually the primaries are short wedged, often with a greater width than length. The apex may become almost cockscomb in outline. Secondary berries become short wedged to even conic. The fruit surface is generally smooth and not rough except for primaries early in the year when some longitudinal folds occur. This variety produces an abundance of pollen in contrast to Goldsmith. The seed formation is therefore more uniform than Goldsmith during wet, cold weather giving the fruit surface a smooth firm appearance.

The calyx of this new variety is quite distinct because of its large size and wide individual sepals that are deeply serrated. The calyx usually joins the pedicel at a point below the surface of the fruit when observing an individual berry in outline from the side. This often gives the calyx a reflexed appearance. The cavity within the fruit is medium to large in size and often light in color especially when the fruit is picked on a three day schedule. The fruit surface color is dark, but not always uniformly colored. The crown crop early in the season in southern California is often unevenly colored. The ability of this variety to produce an abundance of pollen on the anthers of the crown crop is a favorable character in that the earily fruit is well shaped as well as being large and showy with many individual flower stocks being produced from the crown.

This new variety appears to be susceptible to the Two-Spotted Mite, but has as much or more tolerance than Goldsmith. The variety is susceptible to mildew during periods of the year. It has not been completely tested against Verticillium or Red Stele diseases. It shows some tolerance to salty conditions. As a seedling and selection, this variety withstood the natural invasion of certain virus components found in central California without losing its ability to produce.

The varietal characteristics of the novel plant, described below in detail, were observed mainly during the first fruiting season, but reference is also made to their appearance during the second fruiting year. Observations were made in the Watsonville area of California which is a cool coastal area near the Pacific Ocean. The color terminology is in accordance with Ridgeways Color Standards and Nomenclature (1912 edition).

*Plants*

Medium in size, compact, vigorous when given ample chilling before being planted, and has an extensive root system. Normally, multiple crowns are produced by the end of the first growing year.

*Leaves*

Large in size. The central leaflet is usually 7 to 8 cm. in length with the length generally greater than the width. The central leaflet is often ovate in outline. Petioles vary in length, but are mostly short to medium, and mostly 10 to 15 cm. in length. The petioles are comparatively thick in diameter. Petiolules of central leaflets usually average 8 to 10 mm. in length during most of the fruiting season. Bracts are frequently present on the petioles. The leaflet serrations are noticeably deep, acute at the apex and often produce individual serrations that have a double apex. The leaflet surface is rugose and individual leaflets are held in an irregular position. The upper side of mature leaflets is Dark Cress Green, Plate No. XXXI.

*Runners*

Runners are vigorous, but only medium in abundance at the nursery and in the fruiting beds.

*Inflorescence*

The total inflorescence is 20 to 25 cm. long, depending on the time of year. The length of the common peduncle is mainly 8 to 14 cm. secondary peduncles vary from 2 to 3 in number. Primary and secondary berries often ripen at the same time. Tertiary berries are medium to good size, not usually becoming smaller than 25 to 30 mm. in length during the first producing year. Pedicels holding primary berries originate mainly at the axil formed by the union of secondary peduncles. Many inflorescences have secondary peduncles with only one tertiary pedicel originating from them. Some secondary peduncles are actually pedicels as they hold only one berry. Hair on the pedicel 20 mm. below the tertiary flowers lays against and parallel with the pedicel. Flowers are large and may be visible above the plant during the spring and early summer periods. Many flowers have 7 or more petals per flower. Anthers produce an abundance of pollen even during the early spring.

*Fruit*

Crown crop berries are generally large and of high quality, but are not uniform in shape. The primaries of the main crop may be irregular in shape, but fruit from subsequent crops produce primaries of large, short wedged shape in outline with secondaries becoming medium wedged to conic. Tertiaries are mainly conic in outline. Many primaries throughout the season are wider than long, the length averaging 40 to 45 mm. The shoulders are rounded at the calyx end with a calyx often joining the fruit at a point below the surface of the fruit, when observing the outline of the fruit from the side which often gives the calyx a reflexed appearance. The fruit surface of primaries, secondaries and tertiaries is firm and smooth with a high dark gloss and have seeds uniformly spaced. The crown crop primaries and first primaries of the main crop may have longitudinal folds, but subsequent crops produce berries that are smooth and with very few irregularities or seeds that are not fully developed. Seeds are yellow except when the fruit is exposed to full sunlight. The berry has a high dessert quality, but no aroma peculiar to this variety. The fruit surface color is Carmine, Plate No. I. The fresh color near the fruit surface is Scarlet Red becoming Shrimp Pink near the core, Plate No. I.

*Calyx*

Large in diameter with primaries during the summer months averaging 40 to 50 mm. Sepals mostly overlap and are abundant with many serrations present. Sepals are elliptical ovate, or obovate, not narrow and considered wide in comparing with other varieties. The calyx is held generally free of the fruit surface, but may become reflexed. The color of sepals on the side facing the fruit is Varley's Green, Plate No. XVIII.

I claim:

1. The new and distinct variety of strawberry plant herein described and illustrated, and identified by the characteristics enumerated above.

No references cited.

ROBERT E. BAGWILL, Primary Examiner